United States Patent
Kelly et al.

(10) Patent No.: US 8,052,635 B1
(45) Date of Patent: Nov. 8, 2011

(54) ELECTRICAL BREAST PUMP AND FLEXIBLE BREAST CUP SYSTEM

(76) Inventors: Patricia A. Kelly, Burbank, CA (US); Joan P. Ortiz, Burbank, CA (US); Leslie Beckwith, La Mirada, CA (US)

( * ) Notice: Subject to any disclaimer, the term of this patent is extended or adjusted under 35 U.S.C. 154(b) by 741 days.

(21) Appl. No.: 12/130,751

(22) Filed: May 30, 2008

Related U.S. Application Data

(63) Continuation-in-part of application No. 10/644,199, filed on Aug. 20, 2003, now Pat. No. 7,381,197, and a continuation-in-part of application No. 11/656,145, filed on Jan. 22, 2007.

(51) Int. Cl.
*A61M 1/06* (2006.01)

(52) U.S. Cl. .......................................................... 604/74

(58) Field of Classification Search .............. 604/72–76, 604/35, 36, 118; 119/14.01, 14.02, 14.27–14.44
See application file for complete search history.

(56) References Cited

U.S. PATENT DOCUMENTS

| | | | |
|---|---|---|---|
| 4,772,262 A | 9/1988 | Grant et al. | |
| 4,799,922 A * | 1/1989 | Beer et al. | 604/74 |
| 4,961,726 A | 10/1990 | Richter | |
| 5,071,403 A | 12/1991 | Larsson | |
| 5,380,280 A | 1/1995 | Peterson | |
| 5,419,768 A | 5/1995 | Kayser | |
| 5,571,084 A * | 11/1996 | Palmer | 604/74 |
| 5,624,394 A | 4/1997 | Barnitz et al. | |
| 5,676,525 A | 10/1997 | Berner et al. | |
| 5,795,328 A | 8/1998 | Barnitz et al. | |
| 5,810,772 A | 9/1998 | Niederburger | |
| 5,885,246 A | 3/1999 | Ford | |
| 5,902,267 A | 5/1999 | Medo | |
| 5,954,690 A | 9/1999 | Larsson | |
| 6,045,529 A | 4/2000 | Nuesch | |
| 6,383,163 B1 | 5/2002 | Kelly et al. | |
| 6,579,258 B1 | 6/2003 | Atkin et al. | |
| 6,663,587 B2 | 12/2003 | Silver et al. | |
| 2002/0193731 A1 * | 12/2002 | Myers et al. | 604/74 |
| 2005/0043677 A1 | 2/2005 | Kelly et al. | |

FOREIGN PATENT DOCUMENTS

DE 38 20211 A 6/1988

OTHER PUBLICATIONS

Zoppou, Ph.D., Christopher et al., "Comparing Breastfeeding and Breast Pumps Using a Computer Model," J Hum Lact 13(3), Mar. 25, 1997, pp. 195-202.

Vincent, Monte E., et al., "Evaluation of Vacuumi Suction Safety Devices in Preventin Transmission of Human Virus Pathogen." American Clinic Laboratory, Jan. 1989, 4 pages.

(Continued)

*Primary Examiner* — Matthew F Desanto
(74) *Attorney, Agent, or Firm* — Kenneth L. Green

(57) ABSTRACT

A breast pump with a speed, a maximum vacuum, and a minimum vacuum combined with a selectively collapsing breast cup mimics the action of a suckling infant. The speed and maximum vacuum are user selectable to adjust the pump to the particular user. The breast cup is made of a flexible material with a thickness designed to first collapse around the areola area of a breast to mimic an action of a suckling infant.

20 Claims, 13 Drawing Sheets

OTHER PUBLICATIONS

Fewtrell, M.D., Mary S/. "Randomizzed Trial Comparing the Efficacy of a Novel Manual Breast Pump With a Standard Electric Breast Pump in Mothers Who Delivered Preterm Infants," Pediatrics, vol. 107, No. 6, Jun. 2001, pp. 1291-1297.

Blenkharn, J. Jan, "Infection Risks From Electrically Operated Breast Pumps," Journal of Hospital Infection, 1989, 13, 27-31.

Donowitz, Frederic J., "Contaminated Breast Milk: A Source of *Klebsiella* Bacteremia in a Newborn Intensive Care Unit," The University of Chicago, Review of Infectitious Diseases, vol. 3, N9o. 4, Jul.-Aug. 1981.

* cited by examiner

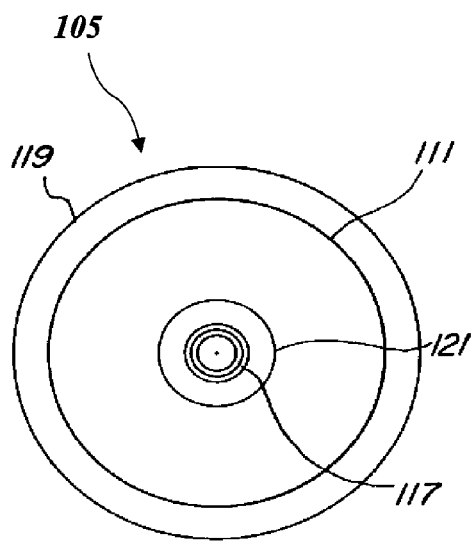
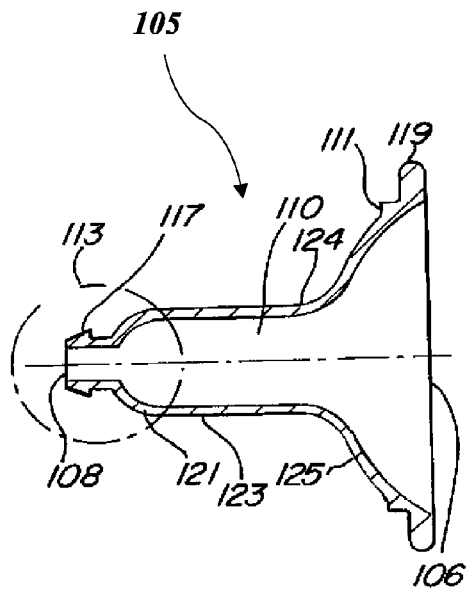
FIG. 11  FIG. 10
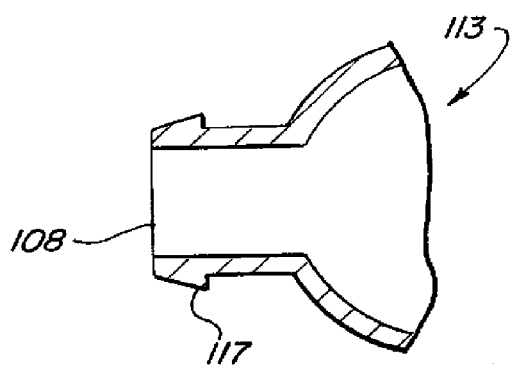
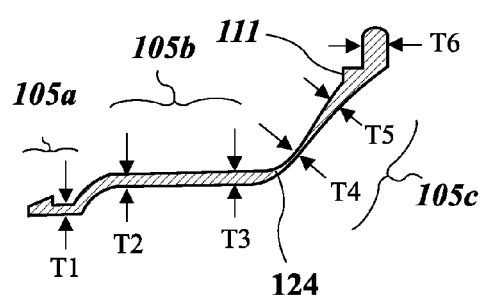
FIG. 12  FIG. 10A

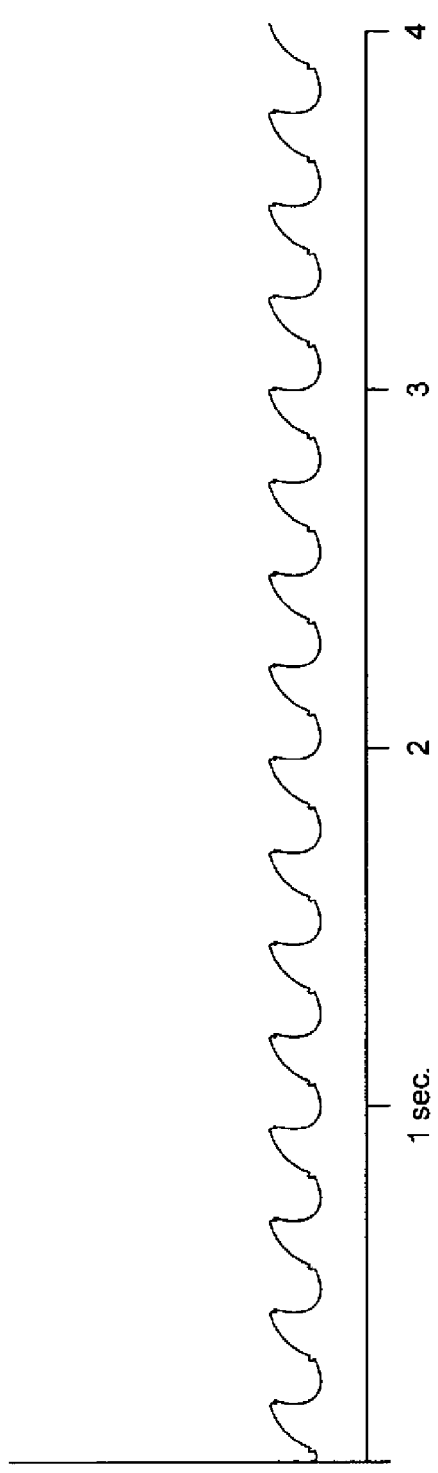
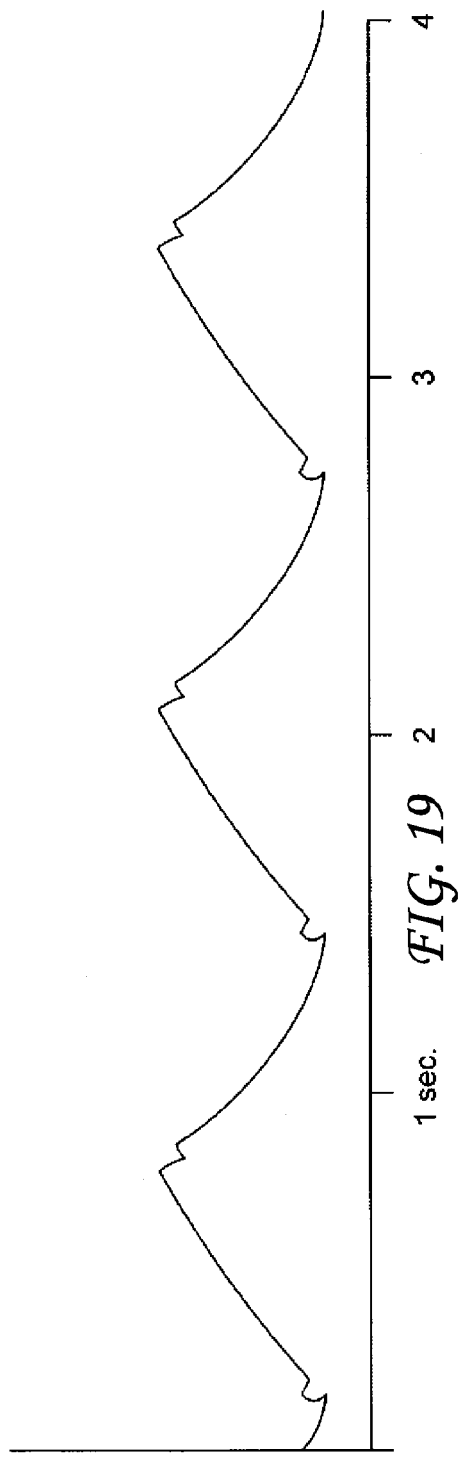

ELECTRICAL BREAST PUMP AND FLEXIBLE BREAST CUP SYSTEM

The present application is a Continuation In Part of U.S. patent application Ser. No. 10/644,199 filed Aug. 20. 2003 and a Continuation In Part of U.S. patent application Ser. No. 11/656,145 filed Jan. 22, 2007, which applications are incorporated in their entirety herein by reference.

BACKGROUND OF THE INVENTION

The present invention relates generally to improvements in breast pumps and more particularly pertains to a combination of an electric pump with improved controls and a flexible breast cup which simulate the action of a nursing infant.

Although the prior art breast pumps and, specifically, the prior art breast pump described and claimed in U.S. Pat. No. 6,383,163 are effective, they also have a number of shortcomings. For example, most prior art breast pumps and breast cup systems only allow a mother to express her milk by applying a uniform vacuum pressure (or vacuum pressure profile) to the face of the breast. This simple approach does not effectively mimic the natural suckling of a nursing infant. As a result, the pump and breast cup system does not extract the milk as efficiently as possible. Consequently, a longer pumping period is required, which increases the physical demands on the mother. These demands may discourage working mothers, or mothers still recovering from childbirth, from thoroughly completing the expression. Incomplete or improper expression of the milk may lead to engorgement of the breasts, mastitis, or infection.

Although the prior art breast pumps and, specifically, the prior art breast pump described and claimed in U.S. Pat. No. 6,383,163 are very effective, these prior art pumps do not contemplate controlling the refractory time of the suction cycle. The result is that the pump is not as efficient as it could be in removing the breast milk. As a result of this decreased efficiency, a longer overall pumping period is required. The longer period increases the physical demands on the user. Moreover, most prior art breast pumps only apply a suction face to the breast for expressing the mother's milk.

In a natural suckling cycle, refractory time of the breast plays an important role in optimizing the efficiency of milk extraction. The refractory time is that part of the nursing cycle that begins after milk has been drawn from ducts within the breast, and ends when the depleted portions of the milk ducts refill. One invention that accounts for this refractory time is disclosed in U.S. patent application Ser. No. 10/644,199, assigned to the assignee of the present invention. The '199 application discloses a breast pump which draws a vacuum in periodic pulses at a frequency that may be adjusted by the mother to track her physiological refractory time.

Nursing an infant, however, is a biological process that is not so easily modeled with mathematical precision. Many conditions can change during expression of the milk. Perhaps the most obvious example is the onset of the let-down, or milk-ejection reflex. Research has shown that prior to let-down, an infant will suck at an elevated rate in the range of 72 to 120 sucks per minute. After let-down, when a satisfactory flow of milk is obtained, the infant relaxes the rate down to around 60 sucks per minute. The vacuum drawn by a suckling infant may vary between 18 mmHg and 200 mmHg. After let-down, an infant typically applies a greater suction force than before let-down. In addition, as the store of milk in the alveoli diminishes, the infant may apply a higher suction force to sustain the flow.

The optimal refractory times, vacuum pressures, and vacuum pressure profiles will vary among different mothers. What is needed, then, is a breast pump that can be easily customized to optimize the efficiency of expression over a wide range of conditions.

BRIEF SUMMARY OF THE INVENTION

The present invention addresses the above and other needs by providing a breast pump with a speed, a maximum vacuum, and a minimum vacuum combined with a selectively collapsing breast cup mimics the action of a suckling infant. The speed and maximum vacuum are user selectable to adjust the pump to the particular user. The breast cup is made of a flexible material with a thickness designed to first collapse around the areola area of a breast to mimic an action of a suckling infant.

In accordance with one aspect of the invention, there is provided a breast pump system including a breast cup, a container, a breast pump, and a control circuit. The breast cup is a collapsible single layer breast cup made of biocompatible material and has an inner surface exposed to vacuum and an outer surface exposed to atmospheric pressure. The breast cup has a connecting portion connectable to a vacuum source, a cylindrical middle area formed contiguous to the connecting portion and configured for receiving a teat of a breast and having a first thickness, and a cone shaped portion formed contiguous to the middle area and configured for receiving a portion of the breast. The cone shaped portion increases in diameter away from the middle area to the large open end and has a second thickness. The second thickness is less than the first thickness so that upon application of vacuum to the connecting portion the cone shaped portion collapses before the mid portion collapses. The container is connected to the breast cup for collecting breast milk. A vacuum line having a first and second end connected to the breast cup provides the vacuum source. The breast pump has an inlet attached to the second end of the vacuum line for drawing a vacuum in the breast cup, thereby causing milk to be extracted from the breast. The control circuit controls a vacuum level provided by the breast pump to the breast cup to establish a pumping rate, a maximum vacuum level, and a minimum vacuum level. The vacuum level increases as a function of the pumping rate until the maximum vacuum level is reached, then the vacuum level drops until the vacuum level is less than the minimum vacuum level, and then the vacuum level increases again as a function of the pumping rate until the maximum vacuum level is again reached. The combination of the collapsing breast cup and the vacuum level and rate controllable breast pump mimics an action of a suckling infant.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein:

FIG. 10 is a cross-section taken along the length of the breast cup preferred embodiment.

FIG. 10A is a cross-section taken along the length of the top half of the breast cup preferred embodiment showing the preferred thickness of the cup at several locations.

FIG. 11 is a front plan view of the breast cup to form the small first end.

FIG. 12 is an expanded view for purposes of illustrating the small first end of the breast cup of FIG. 10.

FIG. 18 is a graph of pressure vs. time, illustrating another example of an actual response of a programmable electric breast pump according to the invention.

FIG. 19 is a graph of pressure vs. time, illustrating another example of an actual response of a programmable electric breast pump according to the invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

The breast pump of the present invention continuously monitors the vacuum pressure that is applied to the milk collection system, i.e., the breast cups, by utilizing an electronic control system that includes a solid state pressure sensor and associated circuitry. The combination of information provided by the sensor completes a feedback loop to the control system, which actuates an electronic valve in the vacuum system to create a suction cycle, with a breast cup with varying thickness resulting in a designed collapse, mimics the action of a suckling infant. In addition, the breast pump is designed to provide fail-safe operation by continuously monitoring the pressure applied to the breast cups, by monitoring the time elapsed during a pumping session, and by monitoring the internal temperature of the control circuits.

Figure 1:
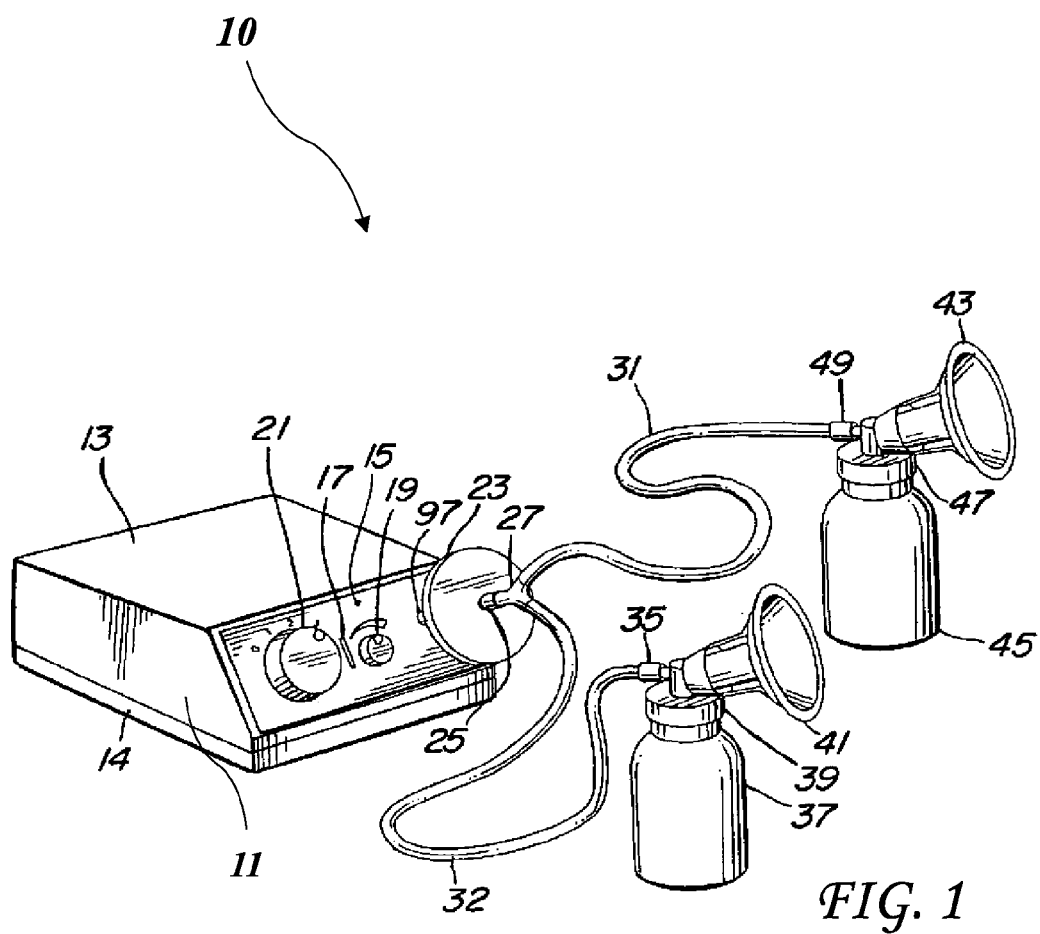
FIG. 1 is a perspective illustration of the basic elements of a preferred embodiment of the electric pump and flexible breast cup of the present invention.

An electronic breast pump system 10 including a user controllable breast pump console 11, and breast cups 41 and 43 and bottles 37 and 45 connected to the pump console 11, is shown in FIG. 1. The pump console 11 of the present invention is illustrated as contained within a housing having a top 13 and a base 14, preferably made of a light-weight plastic. The housing contains a pump control circuit and sensing elements which are hereinafter described. The housing top 13 has manually operable controls for the user such as a vacuum rate selector 21 and vacuum level selector 19. The vacuum rate selector 21 may also include an on/off position. A timer indicating light 17 and on-off fault indicator LED 15 tells the user about the function of the pump console 11. The time indicating light 17 tells the user how much time has elapsed in a session.

A disposable biological isolation filter 23 is shown connected between the breast cups 41 and 43 and a pump connector 97 on the front panel of the housing top 13. The filter 23 is made to be easily connected and disconnected and disposable. It is envisioned that each individual user would have her own set of breast cups and filter 23 which is simply push-connected to the housing unit 13. Further details of the connection of the filter 23 are described hereinafter.

A short length of tubing 25 attaches to an inlet side of filter 23. Because the illustration is for a two breast cup system, a Y-connector 27 connects a tube line 25 to a pair of vacuum lines 31, 32 which lead to respective collection bottles and breast cups. Vacuum line 31 is connected to a breast cup 43 by way of a tube connector 49. Vacuum tube or line 32 is connected to breast cup 41 by way of a tube connector 35. Each breast cup 41 and 43 is symmetrical and made of a soft flexible material, such as silicone rubber and constructed to provide a controlled collapse in operation. Each breast cup 41 and 43 is shaped to comfortably fit over the human teat and a portion of the breast. Each breast cup 41 and 43 is associated with its respective collection bottle 37 and 45. Breast cup 41, besides being connected to vacuum line 32, connects to the interior of the collection bottle 37 by a removable cap 39. Likewise, breast cup 43 is connected to collection bottle 45 by a removable cap 47.

Figure 2:
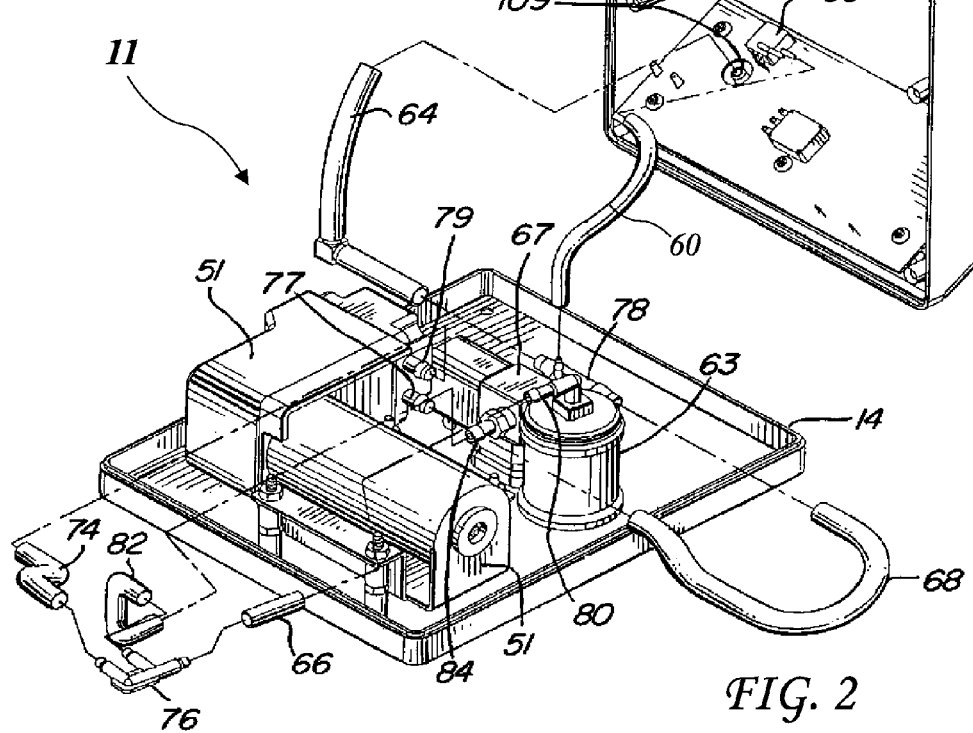
FIG. 2 is a perspective exploded illustration of a preferred embodiment of the pumping and control elements of the present invention.

An exploded perspective of the inside of the housing with the top 13 separated from a base 14, is shown in FIG. 2. A motor-driven vacuum pump 51, preferably a diaphragm vacuum pump but a piston vacuum pump may also be used, is mounted to the base 14 of the housing. An inlet (or vacuum port) 77 of pump 51 is connected by way of vacuum line 68, four-way connector 78 and vacuum line 64 to the back side connection 109 of isolation filter connector 97. Besides connecting vacuum lines 68 and 64 together, four-way connector 78 connects to the inlet side (not shown) of line valve 67. The outlet side 84 of line valve 67 is connected by way of line 82, T-connector 76 and line 66 to the inlet 80 of an exhaust filter 63. The outlet side 84 of the line valve 67 is also connected by way of line 82, T-connector 76 and line 74 to the outlet (or pressure port) 79 of the pump 51. A vacuum sensor 65 mounted to the top 13 of the housing is connected to the four-way connector 78 over line 60, and senses the vacuum level presented to the breast cups 41 and 43.

Figure 3:
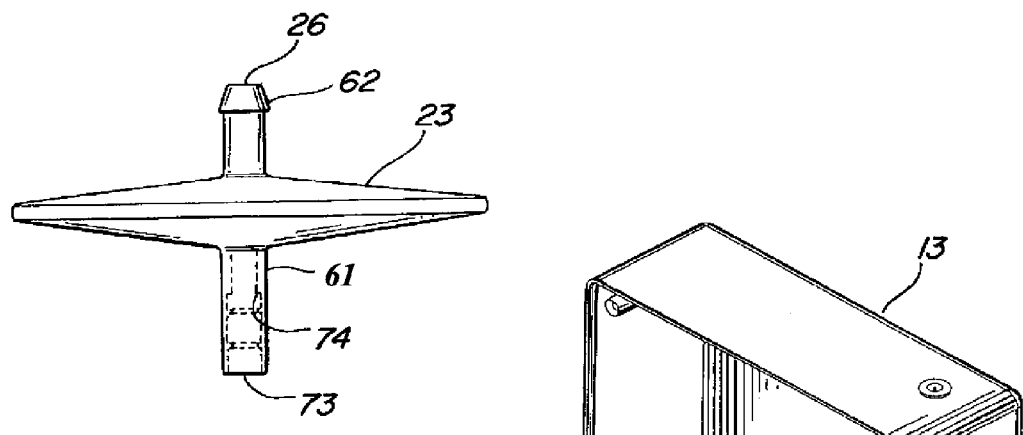
FIG. 3 is a front plan view of a preferred embodiment of an inlet isolation filter used in the present invention.

FIG. 3 illustrates in greater detail the biological isolation filter 23 shown and referred to in FIG. 1. Biological filter 23 is contained within a polypropylene housing which is preferably rated at 15 psi or better. The filter is unidirectional in that air flows only from the inlet side 26 to the outlet side 73. The inlet side preferably contains a quarter-inch single hose barb connector 62. The outlet side 73 is a cylindrical extension 61 with a step-down interior diameter creating a ledge 74 on the inside. The filter media utilized for biological filter 23 is preferably approximately 1.0 micron polytetrafluorethylene (PTFE) and the filter is preferably approximately 60 mm in diameter.

Figure 4:
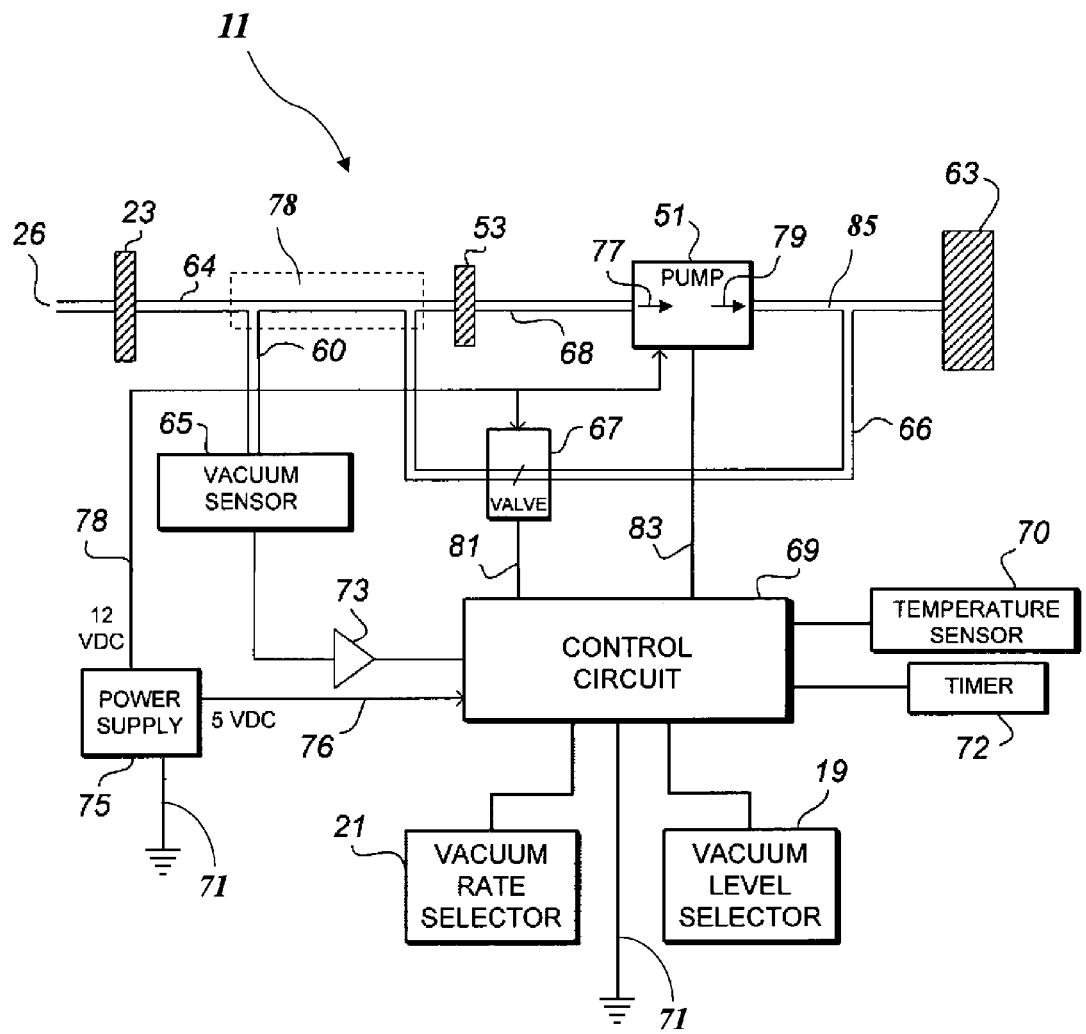
FIG. 4 is a block diagram including the pumping and control elements of the present invention
Figure 5:
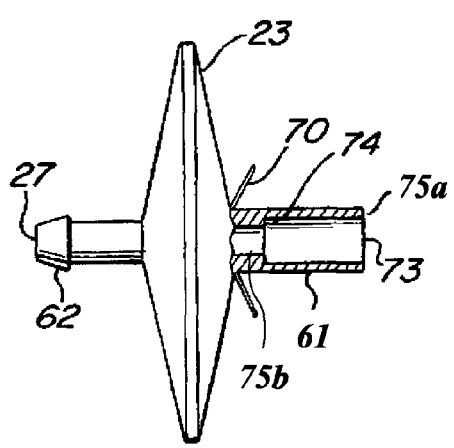
FIG. 5 is a plan view, partially broken away of the inlet isolation filter.

A block diagram shown in FIG. 4 illustrates the connection of mechanical and electrical components within the pump console 11 (see FIG. 2). Electrical power for the system is provided by a power supply 75. In the embodiment shown, power supply 75 provides two DC outputs: a 5 VDC output for powering the active electronics within a programmable control circuit 69, and a 12 VDC output. The 12 VDC output is for powering the pump 51 and the electrically operated valve 67. Power supply 75 may be a battery bank, or an AC/DC converter receiving power from a standard 120 VAC outlet. In another embodiment, power supply 75 may include a battery charger coupled to a bank of rechargeable batteries, or a battery holder that holds one or more standard commercial batteries such as ten AA batteries.

The programmable control circuit 69 provides central control for the system. The control circuit 69 may be a microprocessor, microcontroller, FPGA, ASIC, or the like, and may include integral memory for storing executable control algorithms. The control circuit 69 may receive up to five input signals. Two of the input signals are control inputs from the vacuum level selector 19 and the vacuum rate selector 21. The vacuum rate selector 21 provides a desired pump rate signal to control circuit 69, and may include an on/off function which turns the system on or off. The vacuum level selector 19 provides a desired maximum vacuum input to control circuit 69. The desired signals may be a voltage that varies continuously or in discrete steps according to a selector 19 and 21 positions.

Two additional inputs may include a vacuum measurement from the vacuum sensor 65 and temperature measurement from a temperature sensor 70. The vacuum sensor 65 senses vacuum in vacuum line 64 through conduit 60, and provides a signal representing the sensed vacuum to the control circuit 69. An example of a suitable vacuum sensor 65 is a silicon packaged piezoresistive pressure sensor or the like, for example, a Fujikura type XFHM vacuum sensor. The temperature sensor 70 senses temperature within the housing of the pump console 11 and provides a signal representing the sensed temperature to control circuit 69. If the sensed temperature is an abnormally high or unsafe operating temperature, or If the sensed temperature exceeds a predetermined maximum safe operating temperature, the control circuit 69 may stop the pump 51, or otherwise shut down the operation of the breast pump system. One example of a suitable temperature sensor 70 is an integrated circuit type LM50C sensor manufactured by National Semiconductor.

Another input to the control circuit 69 may be a timing or clock input provided by a timer 72. The timer 72 may be a well-known type and is not described herein in further detail. The timer 72 may be integral into control circuit 69 or be a separate device. The timer 72 provides a clock input which may be used to synchronize the operation of control circuit 69, and to provide a means for control circuit 69 to measure elapsed times.

The control circuit 69 preferably provides two output signals. The first output signal may be a pump drive signal carried on line 83 to the pump 51. The pump drive signal generated by the control circuit 69 preferably varies according to the position of vacuum rate selector 21. As the selector 21 is adjusted to increase vacuum, control circuit 69 responds by outputting a drive signal which causes a commensurate increase in vacuum (or suction rate) in line 68 created by the pump 51 (e.g., increase in pump operating speed). The pump 51 is preferably a DC pump and receives a pulse width modulated DC power signal to control pump speed, for example, a square wave drive signal having a variable pulse width, or duty cycle. When vacuum rate selector 21 is switched on and to a minimum position, control circuit 69 may provide a fractional square wave, such as square wave having a 50% duty cycle to the pump 51. With vacuum rate selector 21 at a maximum position, control circuit may provide a 100% duty cycle signal to the pump 51. Intermediate position of vacuum rate selector 21 may cause a corresponding adjustment in the duty cycle of the drive signal. Other drive signals may be used, such as a DC signal having a voltage that varies according to selector position, or an AC pulse having a shape other than square. In a preferred circuit, the power supply 75 provides a constant +12 VDC source to the pump 51 and the control circuit controls grounding of the pump 51 to ground 71.

The vacuum line 68 is connected to the inlet (or vacuum port) 77 of the pump 51. The biological isolation filter 23 is serially connect to vacuum line 68, and thus the pump 51, through the vacuum line 64 and the four-way connector 78. The inlet 26 of biological filter 23 is connected to breast cups 43 and 41 (FIG. 1) by way of their respective vacuum lines 31 and 32. Under the control of the control circuit 69, the pump 51 varies its speed accordingly, causing the vacuum (or suction rate) at inlet 77 to vary in proportion to the position of vacuum rate selector 21.

A second biological filter 53 may be serially connected to or in-line with the vacuum line 68 between the inlet 77 of the pump 51 and the four-way connector 78. The filter 53 serves to reduce pumping noise which has been observed with some pumps 51, and also may be included to isolate the vacuum pump 51 from the valve 67 in case of valve failure, but is not required for operation. The exhaust filter (or muffler) 63 is connected to the outlet 79 of pump 51 by a pressure line 85 and the outlet line 66 of vacuum relief valve 67 T's into the line 85 between the pump outlet 79 and the filter 63. The vacuum line 66 connects or shunts around the pump 51 from the inlet side of biological filter 53, through the vacuum relief valve 67, connecting to the outlet side of the pump 51 between the pump 51 and the inlet side of the exhaust filter 63. The exhaust filter 63 prevents dispersal of aerosols and contaminants in the atmosphere surrounding the pump and thereby reduces the possibility of cross-contamination.

The vacuum relief valve 67 is connected into the shunt vacuum line 66 to provide a means for bypassing the pump 51. Valve 67 is controlled over line 81 by control circuit 69. The valve 67 may assume either an open state or a closed state. When the pump 51 is running and control circuit 69 causes valve 67 to close, vacuum increases in vacuum line 64 and in breast cups 41 and 43. When control circuit causes valve 67 to open, the pump 51 is bypassed, and vacuum in vacuum line 64 begins lowering to an ambient pressure level at exhaust filter 63.

The signal transmitted from vacuum sensor 65 may be amplified by a sensor amplifier 73 before being input to control circuit 69. Normal operation of the breast pump is controlled according to the positions of vacuum rate selector 21 and vacuum level selector 19, and on feedback received by control circuit 69 from vacuum sensor 65.

The function of the breast pump in the housing is to provide a desired vacuum at male connector 97 to which the biological isolation filter 23 is removably connected. The vacuum lines connected to the biological isolation filter 23 carry the vacuum to the breast cups. The breast pump system may be started by switching vacuum rate selector 21 from an off position to an on position.

At startup, control circuit 69 causes valve 67 in vacuum line shunt 66 to be held open for a short time (counted by timer 72) so that the vacuum circuit is open to the atmosphere through exhaust filter 63. This prevents a vacuum level from being built up instantaneously. Also at startup, control circuit 69 controls the pump 51 according to the position of vacuum rate selector 21. Within a second or two after startup, control circuit 69 closes valve 67. With the breast cups positioned against a user's breasts, and with the vacuum lines 31 and 32 attached to the pump by way of the first biological isolation filter 23, the vacuum circuit for the system is closed. The pump 51 then draws a vacuum in the system. The vacuum sensor 65 attached to the vacuum line 64 continuously monitors the level of vacuum in the system. The vacuum sensed by sensor 65 is a good indicator of the vacuum being applied to breast cups 41 and 43. When the vacuum level reaches a maximum level set by the vacuum level selector 19, control circuit 69 causes valve 67 to open for a short period of time (counted by timer 72) to cause the vacuum level in breast cups 41 and 43 to drop. When the vacuum pressure has dropped to a level at or below a minimum vacuum level, control circuit 69 will cause valve 67 to again close, thereby allowing the vacuum to increase again. In this fashion, control circuit 69 cycles the vacuum at the breast cups in response to the combined selected vacuum rate signal and the selected vacuum level signal, thereby mimicking a suckling infant. This cycle repeats until the unit is turned off completely.

In one embodiment, the minimum vacuum level is a predetermined value stored in the memory of control circuit 69. In another embodiment, the minimum vacuum level changes as a function of the maximum vacuum level set by the vacuum level selector. In another embodiment, control circuit 69 sets the minimum and maximum vacuum pressures according to data stored in a lookup table. In yet another embodiment, the control circuit 69 calculates the minimum and maximum vacuum pressures by executing an algorithm.

The cycling of valve 67 on and off repeats until the electronic breast pump system 10 is turned off by adjusting vacuum rate selector 21 to the off position. During the time that valve 67 is closed and the vacuum rate selector is turned on, increasing vacuum is applied to the portion of the breasts contained within the flexible breast cups 41 and 43. During the time that valve 67 is open, decreasing vacuum is applied to the breasts until a minimum vacuum is reached. Thus, by cycling valve 67 open and closed, control circuit 69 creates a cycling of vacuum within breast cups 41 and 43. With vacuum level selector 19 and vacuum rate selector 21 in fixed positions, a periodic vacuum cycle results. The vacuum cycle includes a vacuum period and a refractory period. Vacuum is drawn during the vacuum period and vacuum is relieved during the refractory time.

The control system of the present invention allows a user to synchronize the vacuum cycle with the physiological refractory time which is inherent in the normal function of a lactating breast. The physiological refractory time is that part of a feeding or pumping cycle which starts after the milk has been ejected from the breast and ends when the breast chambers are refilled with milk prior to the next ejection of milk. Synchronization of the vacuum cycle of the electronic breast pump system 10 to the natural refractory time of breast may be achieved by a user adjusting vacuum level selector 19 and vacuum rate selector 21 until an optimal milking rate is achieved, i.e. when the refractory time is in phase with the natural refractory time to allow the breast chambers to refill in time for the next vacuum pulse. The result is a substantial increase in the expression rate of milk, and a concomitant reduction in physical demands on the mother.

The refractory time is a function of both the vacuum level set by vacuum level selector 19, and vacuum rate set by vacuum rate selector 21. The refractory time is the period from the end of a vacuum pulse applied by the control circuit 69 to valve 67 that causes the valve to open to relieve vacuum in the breast cup, to the beginning of the next vacuum pulse. When the next vacuum pulse is applied by the control circuit, the valve closes and vacuum pressure increases. The duration, Pv, of the vacuum pulse is the time required for the pump 51 to raise vacuum pressure in the system from the minimum level to the selected maximum level.

With vacuum level selector 19 in a fixed position, Pv may be shortened by raising the vacuum rate, i.e. by selecting a higher rate on vacuum rate selector 21, or Pv may be lengthened by lowering the vacuum rate on vacuum rate selector 21. Conversely, with vacuum rate selector 21 in a fixed position, Pv may be lengthened by raising the vacuum level, i.e. by selecting a higher maximum vacuum on vacuum level selector 19, or Pv may be shortened by lowering the maximum vacuum level on vacuum level selector 19. Thus, a user may "tune in" an optimal refractory time by connecting the breast cups, turning the system on, and adjusting one or both selectors until the an optimal expression rate is achieved. It has been found that the ability of the user to adjust the refractory time, to suit the individual physiological differences of the user, adds considerably to the comfort level of the user. The vacuum cycle may be adjusted by the user in a preferred range of 28 to 250 cycles/minute, and more preferably 32 to 70 cycles/minute.

The control circuit 69 contains, or is coupled to, the timer 72 which may provide timing pulses for control circuit synchronization and other counting functions. One such counting function is a time-out function that provides a safety feature for a user. A counter (not shown) within control circuit 69 may start counting the first time the vacuum sensed by vacuum sensor 65 reaches the maximum level set by the vacuum level selector. The start of the count may be indicated on the front panel display 17. The display on the front panel may assist the user in remembering not to exceed the recommended amount of time for one session of expressing milk using the breast pump system. In one example, the recommended amount of time at one sitting should not exceed 20 minutes. The timer in control circuit 69 is reset when the system is powered off.

Timer 72 may provide diagnostic functions as well. In one embodiment, a controller (e.g. control circuit 69) may count the time elapsed on timer 72 between closing valve 67 and reopening valve 67 within a single cycle. If the time elapsed is less than a predetermined minimum closure time, the controller may stop the vacuum pump. Such a condition is a likely indication of an obstruction somewhere in the pneumatic lines. In another embodiment, if the time elapsed is greater than a predetermined maximum closure time, the controller may stop the vacuum pump. This condition is a likely indication of a leak somewhere in the pneumatic lines. In these embodiments, the predetermined minimum and maximum closure times may be stored in a memory accessible by the controller, or programmed into an algorithm executed by the controller.

Another safety feature that may be provided by control circuit 69 is a low pressure shut-off threshold, or equivalently, a maximum vacuum pressure threshold. The low pressure shut-off threshold may be permanently fixed or programmed into control circuit 69, at a vacuum pressure higher than the highest maximum vacuum pressure obtainable using vacuum level selector 19. When the low pressure shut-off threshold is sensed by vacuum sensor 65, control circuit 69 shuts down the pump. This safety feature would actuate, for example, if valve 67 fails closed, if the pump 51 runs at an excessive speed, or if for some other reason vacuum pressure cannot be relieved in the system.

The vacuum cycle created by the breast pump system 10 is ideally suited for use with breast cups 41 and 43 which collapse in a progressively controlled way which simulates the suckling action of a nursing infant. Progressively collapsible breast cups collapse in response to an applied vacuum such that the areola area of the breast is squeezed before the teat. Breast cups of this type are disclosed in co-pending U.S. patent application Ser. No. 10/644,199 incorporated by reference above.

Referring now to FIGS. 5, 6, 7 and 8, the easy insertion and removable feature associated with the biological filter 23, is illustrated. The unidirectional flow filter 23 connects to the pump 51 by way of a quick connect and release mechanism that is vacuum tight. The outlet end 73 of filter 23 has a cylindrical extension 61 broken away at line 70, to show the two distinct internal diameters creating a ledge 74 at the interface between the larger diameter 75a at the outlet end 73 and the smaller diameter at the filter end 75b.

Figure 6:
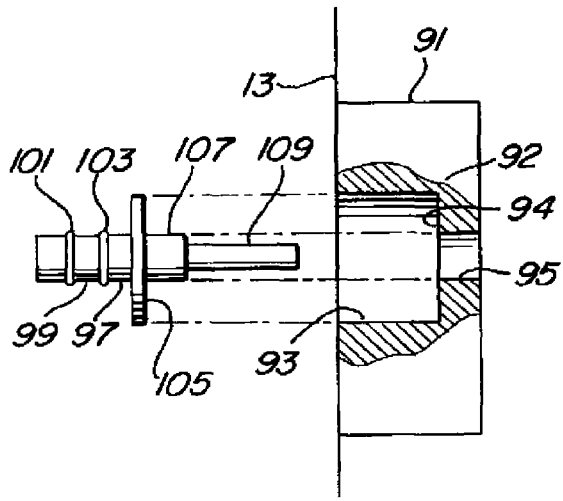
FIG. 6 is an exploded view, partially broken away, of the inlet isolation filter connector mounted in the pump housing.
Figure 7:
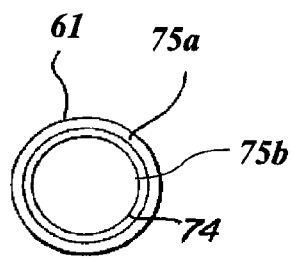
FIG. 7 is an end view of the filter of FIG. 5.
Figure 8:
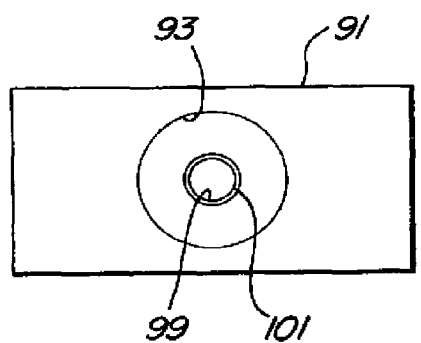
FIG. 8 is a front plan view of the filter connector of FIG. 6.

A connector block 91 is mounted to the underside of the face plate on the top 13 of the housing. The connector block 91 of FIG. 6 is broken away at 92 to show the two diameter pass-through apertures in the block 91. The larger diameter cylindrical aperture 93 defines the size of the aperture in the face plate of the housing. The smaller diameter cylindrical aperture 95 extends from the larger diameter aperture to the other side of the connector block 91. The difference in diameter between the two, creates a mounting ledge 94 in the larger aperture 93 of the connector block 91.

A male connector 97 is mounted inside the cylindrical aperture 93 of the connector block 91 against the mounting ledge 94. FIG. 6 shows the male connector 97 outside of the connector block for clarity of illustration. In assembled form, the shaft 99 of connector 97 is located within cylindrical aperture 93 with the mounting ring 105 of the male connector 97 fastened against ledge 94 in any convenient manner. The backside 107 of shaft 99 on the other side of mounting ring 105 extends through cylindrical aperture 95 to the other end of the connector block 91. The backside 107 of the connector 97 is stepped down to a smaller diameter cylinder 109 for connection to the vacuum lines 64 inside the housing.

The filter 23 attaches to the connector 97 inside the connector block 91 by fitting the cylindrical extension 61 of the filter 23 over the shaft 99 of the male connector 97. To insure a vacuum-tight fit between the filter 23 and the male connector 97, a pair of O-rings 101 and 103 of appropriate size are displaced along the length of the shaft 99. In addition, the shaft extension is preferably tapered at about six degrees (6.degree.) from its base at the mounting ring 105 to the tip. Furthermore, the inside O-ring 103 may be slightly larger in diameter than the outside O-ring 101. The result of this structure is a quick connect/disconnect connection which becomes tighter as the vacuum level increases. As the vacuum goes up, cylindrical extension 61 of the filter 23 is pulled further along the shaft 97 of the connector 97 to the mounting, creating a tighter fit.

When a user desires to make a connection between the collection system and the vacuum pump inside the housing, cylindrical extension 61 is simply inserted over shaft 99 of male connector 97 which is mounted inside of the connector block 91 on the panel of the housing. The two O-rings 101 and 103, along with the tapered shaft extension, insure that the connection is vacuum tight even though the filter may be easily inserted and removed. This structure also enables easy replacement of the filter.

The breast pump system 10 of the present invention is constructed to utilize a plurality of separate and individualized milk capture systems, each one isolated by their respective separate filters, in order to protect the individual user and prevent contamination between the equipment and the user. The filters utilized are inserted into the vacuum line between the collection bottles and the pump 51. The first and perhaps most important filter is the filter 23 which functions to isolate the milk and the user from the pump console 11. The importance of this biological isolation has been studied and chronicled in a variety of scholarly articles such as the article entitled "Contaminated Breast Milk: A Source of Klebsiella Bacteremia in a Newborn Intensive Care Unit," Volume 3, No. 4, of Reviews of Infectious Diseases, July/August 1981; "Infection Risks From Electrically Operated Breast Pumps" in Journal of Hospital Infection 1989; and "Evaluation of Vacuum Suction Safety Devices in Preventing Transmission of Human Virus Pathogens" in American Clinical Laboratory, January 1989.

The breast pump of the present invention is unique in this industry in that the pressure that is applied to the milk collection system, i.e., the breast cups, is continuously monitored, utilizing an electronic system composed of a solid state pressure transducer and its associated circuitry. The information provided by the transducer causes the logic circuits to control an electronic valve in the vacuum system. Furthermore, the breast pump is designed to provide fail-safe operation by continuously monitoring the pressure applied to the breast cups.

Figure 9:
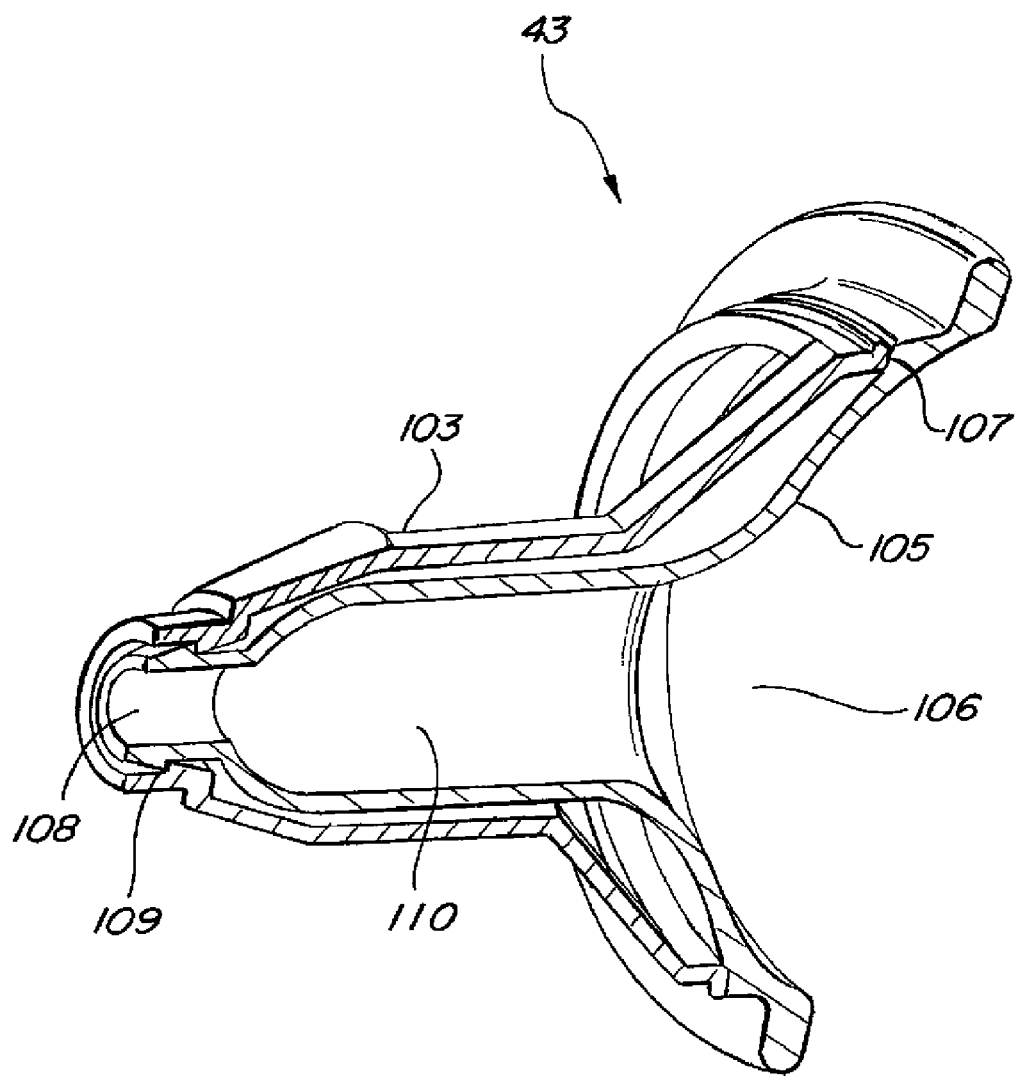
FIG. 9 is a cut-away sectional perspective illustration of a preferred embodiment of the breast pump.

A preferred embodiment of a breast cup 43 is illustrated in FIG. 9 as a two-part assembly of a molded holder 103 and a breast cup 105 which is held within the molded holder 103 at a larger second end 107 of holder 103 and at a smaller first end 109 of holder 103. The holder 103 is preferably made from a plastic material and more preferably from polycarbonate material molded to the preferred shape shown. The breast cup 105 is preferably molded from a biocompatible silicone material which is flexible. The large second end opening 106 of the breast cup of FIG. 9 is sized to accept a portion of a human breast for many different sized women with the teat of the breast extending into the narrow middle area 110 of the breast cup 105. The small opening 108 in the first end of the breast cup 43 is designed for fastening to a vacuum line. When a vacuum is pulled at opening 108, the breast cup 105 will collapse in a controlled progressive manner that mimics a suckling infant, as will be explained hereinafter.

Referring now to FIG. 10 which shows a cross-section of the breast cup 105 along its length, the structure of the breast cup is more readily illustrated. The first end opening 108 has a cross-sectional diameter of approximately one half inch or less, as shown by the exploded Section 113 in FIG. 12. A wedge-type ridge 117 is formed at the extreme end. The ridge 117 interacts with a complementary ridge 109 on the inside of the holder 103 as shown in FIG. 9. The first end is preferably about 0.175 inches thick, providing fairly rigid support for the fastening wedge 117. At the first radius 121, the cross-sectional diameter of the breast cup 105 increases to about one inch. The wall thickness at this point remains about the same. The wall thickness remains constant to the next radius 124. The length of the cup from the small first end opening 108 to radius 124 is about two-thirds the length of the entire cup 105. At the radius 124, the cup size expands in a cone-shape manner to the second and large open end 106 which is approximately 3.5 inches in diameter. The open end 106 has a thickened ridge 119 defining its outer perimeter which adds stability to the second end of the breast cup. Adjacent to the ridge 119 is a platform 111 which forms a stable base for the second end 107 of the holder 103 (FIG. 9) to rest on.

The thickness of the wall of the cup at point 125, just beyond the radius 124, where the cup 105 enlarges in a cone-shaped manner is chosen to be less than the thickness of the walls at 123 and at the second end 119. As a result of this cross-sectional wall thickness variation, when a vacuum is applied to the opening 108 at the first end of the cup 105, the cup 105 will collapse first at area 125 near the platform 111 on the cup 105 which is located on the areola area of the human breast when the human breast is located in the cup 105, and then progressively collapse towards the radius 124. The collapse of cup 105 in this manner causes the areola of the human breast to be squeezed first, and then the teat which is located in the center 110 of the elongated section (or cylindrical middle area) between radius 121 and radius 124 of the breast cup. This controlled collapse replicates the mechanical forces of a suckling infant and causes the expression of milk in a more efficient and comfortable manner.

A cross-section taken along the length of the top half of the breast cup 105 showing the preferred thicknesses of the cup at several locations is shown in FIG. 10A. The thickness T1 in a connecting portion 105a is preferably approximately 0.15 inches, the thicknesses T2 and T3 in a cylindrical middle area 105b are preferably approximately 0.1 inches, the thickness T4 in a cone shaped portion 105c just beyond the radius 124 is preferably approximately 0.03 inches, the thickness T5 of the cone shaped portion 105c approaching the platform 111 is preferably approximately 0.1 inches, and the thickness T6 of the thickened ridge 119 is preferably approximately 0.2 inches. The thickness tapers smaller through the radius 124 to the smallest thickness T4 just after the radius 124, and then tapers larger from the smallest thickness T4 to the thickness T5 just before the platform 111. This tapering provides the progressive collapse of the breast cup 105 when vacuum is increased. The smallest thickness T4 is preferably approximately ⅓ the thickness of the cylindrical middle area 105b and of the cone shaped portion 105c just before the platform 111.

Figure 13:
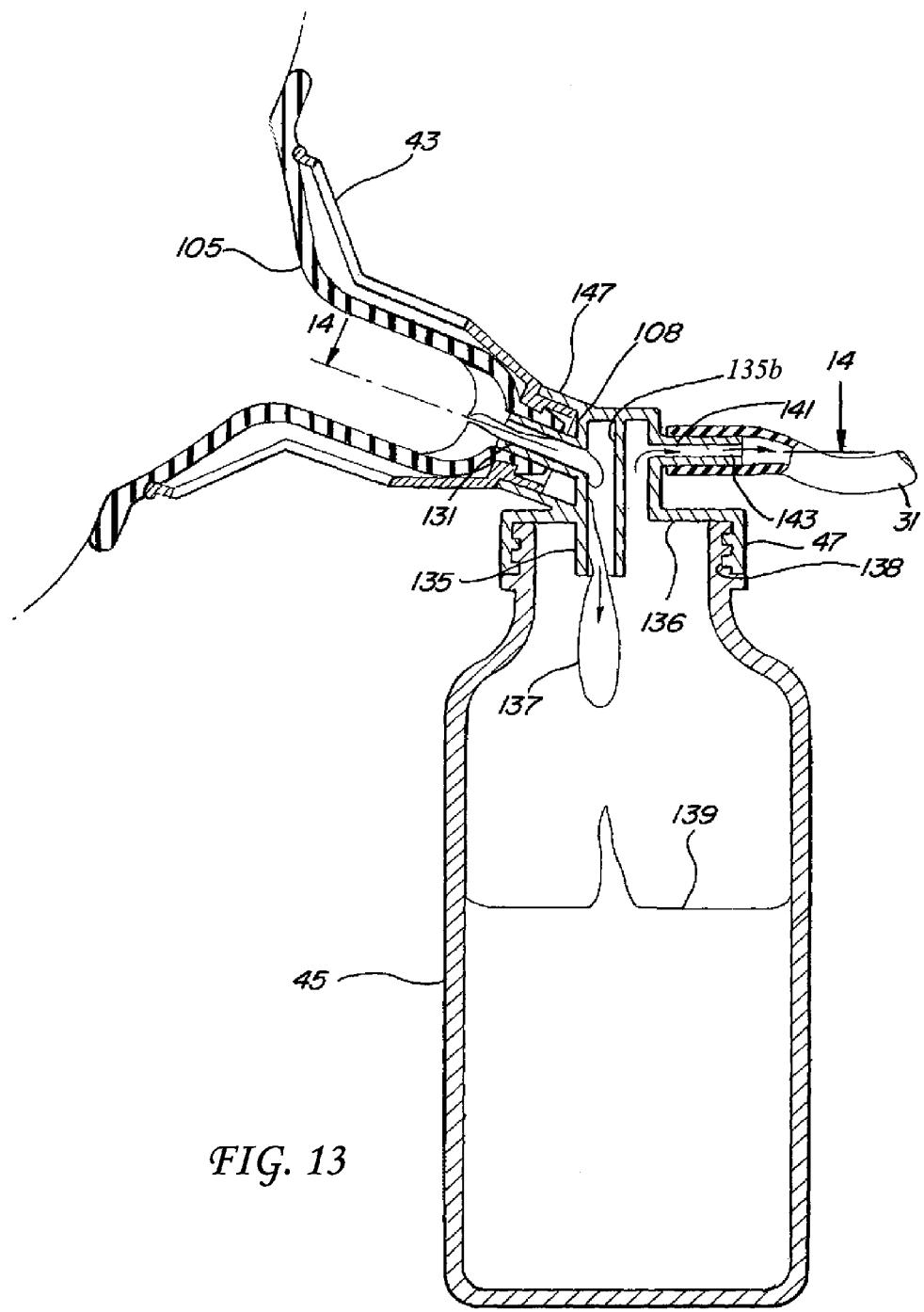
FIG. 13 is a cross-sectional view of a cup connected to a bottle cap pursuant to a preferred embodiment of this invention.
Figure 14:
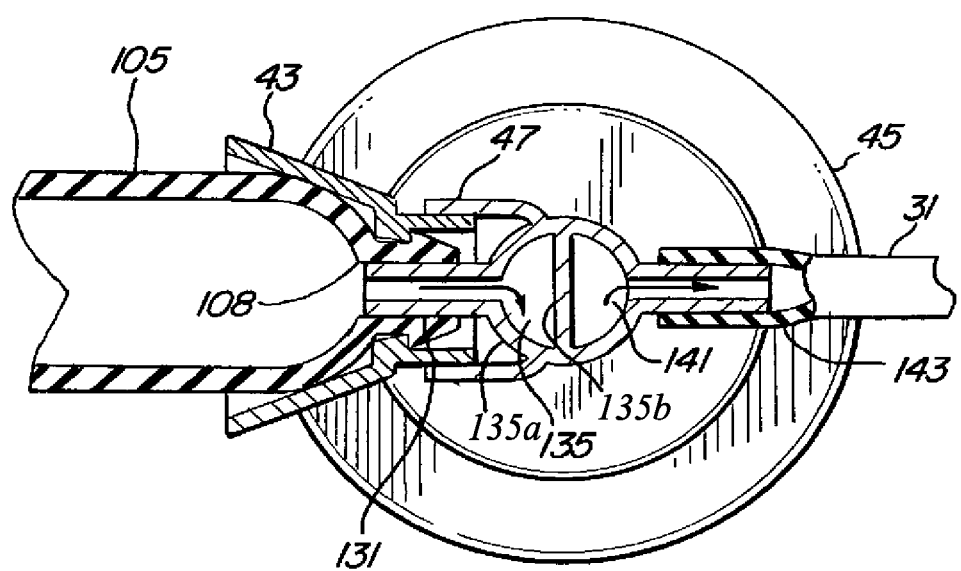
FIG. 14 is a cross-section along lines 14-14 of FIG. 13 showing the preferred construction of the bottle cap.

Referring now to FIGS. 13 and 14 which illustrate in greater detail the bottle cap 47 for the milk collection bottle 45, the breast cup 43 is shown connected to female receptacle 147 on cap 47. Vacuum tube 31 is shown connected to male tube connector 143. The narrow discharge end of the flexible cup 105 has an opening 108 therein which receives the hollow male extension 131 located in receptacle 147, when the narrow end of the breast cup assembly 43 is inserted into receptacle 147. The result is a vacuum-type connection between the breast cup 105 and the collection bottle 45.

The other end of the hollow male extension 131 connects to a hollow tube 135 which, in its preferred embodiment, is semi-circular in shape with one wall 135b being flat and the other wall 135b being rounded. Tube 135 extends down below the surface of the closed end 136 of cap 47 which has internal threads 138 located therein to engage external threads on the bottle 45.

The length of tube 135 below the closed end 136 is chosen so that the separation between the discharge end of tube 135 which discharges the mother's milk 137 into the bottle 45 is a sufficient distance away from the opening of tube connector 143 so that there is no splash back into tube connector 143 of the mother's milk 137 dropping into bottle 45, or any milk 139 contained in the bottle splashing up into the opening of tube connector 143.

In operation, the breast pump creates a vacuum in vacuum line 31 causing evacuation of all air 141 contained in bottle 45 and air contained in breast cup 105 between its discharge opening 108 and the other end when it is closed by a human breast. The vacuum in both the bottle 45 and in the breast cup 105 causes external forces to collapse cup 105 according to the vacuum cycle selected. As explained hereinabove, this cycle creates the mechanical forces of a suckling infant that causes the expression of the mother's milk 137 into the collecting bottle 45. The design of the cap 47 as shown in FIGS. 13 and 14 specifically prevents any contamination of the vacuum system by the mother's milk 137 being expressed into the bottle, or the milk 139 contained in the bottle, being pulled into the vacuum tube connector 143.

Figure 15:
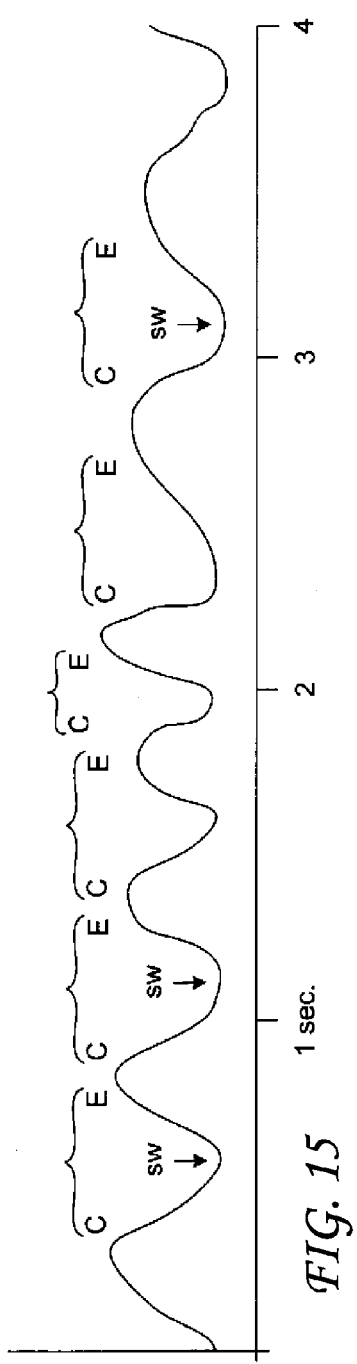
FIG. 15 is a graph of pressure vs. time, illustrating a typical natural respiratory cycle of a nursing infant.

FIG. 15 shows a respiratory cycle of a suckling infant. The graph is based on information recorded in Weber, et al., "An Ultrasonic Study of the Organisation of Suckling and Swallowing by Newborn Infants," Developmental Medicine & Child Neurology, 1986. The horizontal axis indicates time. The vertical axis indicates pressure, where a rising segment corresponds to pressure building in the areola as the infant inspires, drawing a suction on its mother's breast. The rising segment may also represent the natural refractory time of a lactating breast. A falling segment indicates a pressure reduction in the areola as milk is drawn out while the infant expires. Each trough, indicated by SW, corresponds to a time when the infant swallows the milk. Points labeled C correspond to times when the mother's nipple begins to compress. Points labeled E correspond to times when the nipple is fully expanded.

As indicated in FIG. 15, the respiratory cycle (or suck-swallow cycle) of a nursing infant exhibits periodic behavior. The four-second trace shown in the figure was derived from a test conducted by Weber et al., in which the infant under test completed 26 suck-swallow cycles in 15 seconds. This example indicates a typical respiratory cycle between about 100 and about 120 cycles per minute. Actual respiratory cycles may vary within this or some other range, depending on the natural refractory time of the mother, and may also vary for each mother-infant pair. Generally, the respiratory cycle closely tracks the natural refractory cycle of the mother's lactating breast during nursing.

Figure 16:
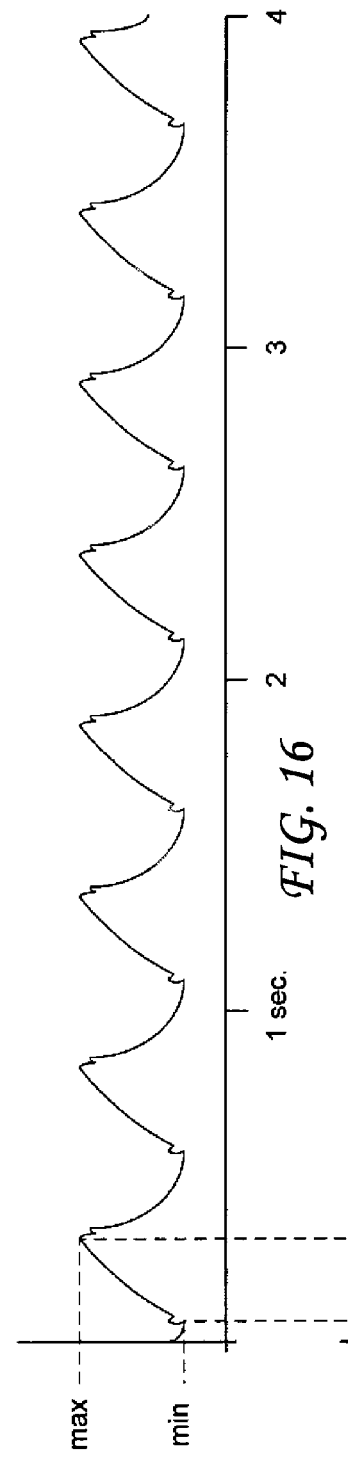
FIG. 16 is a graph of pressure vs. time, illustrating one example of an actual response of a programmable electric breast pump according to the invention.

FIG. 16 illustrates one example of an actual measured response of a programmable electric breast pump according to the invention. In this figure, the horizontal axis indicates time, and the vertical axis indicates vacuum. A higher level in the vertical direction indicates greater vacuum (i.e., greater negative pressure). The response is a periodic vacuum pulse applied to the breast cups, where the maximum peak corresponds to the selected maximum vacuum level. The negative peak corresponds to a minimum vacuum level that may be pre-programmed, or that may be calculated as a function of the selected maximum. In this example, the breast pump controls (vacuum level selector 19 and vacuum rate selector 21) are set to synchronize the periodic vacuum pulse to the natural refractory time illustrated in the example of FIG. 15.

Figure 17:
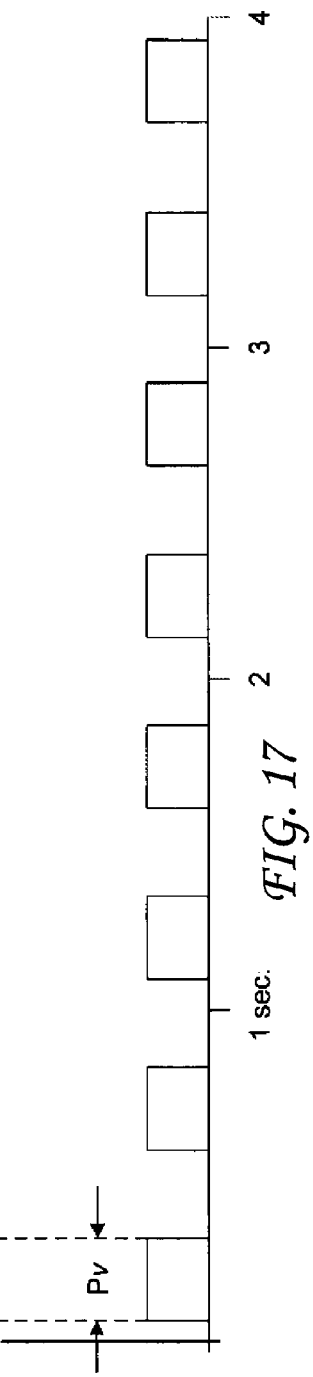
FIG. 17 is a graph of voltage vs. time, illustrating one example of square wave input to a vacuum pressure relief valve in a system according to the invention.

The periodic vacuum pulse as illustrated in FIG. 16 may be achieved by control circuit 69 actuating vacuum relief valve 67 each time vacuum sensor 65 senses a maximum or a minimum vacuum pressure. The square wave shown in FIG. 17 shows an example of an electronic pulse applied to valve 67 by control circuit 69 used to create the periodic vacuum pulse of FIG. 16. The duration of the electronic pulse applied to valve 67 lasts for a time period Pv, which corresponds to the duration of the rising edge of the periodic vacuum pulse, as shown. When vacuum sensor senses a maximum vacuum pressure in the breast cups, it sends a signal to control circuit 69 to remove the electronic pulse from valve 67, and the vacuum level drops until it reaches the minimum. At that point, vacuum sensor 65 alerts control circuit 69, and another electronic pulse is applied to valve 67. The frequency of the pulse in this example is approximately 120 cycles per minute. The maximum vacuum level is about 80 mmHg and the minimum vacuum level is about 20 mmHg. With such a control scheme, an electronic breast pump of the present invention maintains vacuum in the breast cups equal to or greater than the minimum level at all times. This ensures that sufficient suction is maintained in the breast cups to keep them in place against the breasts during a milking session.

FIG. 18 illustrates another periodic vacuum pulse achieved using the same breast pump, by changing the control setpoints. In this example, the frequency of the periodic vacuum pulse is as least twice that of FIG. 16. With the setpoint of vacuum rate selector 21 unchanged from its setting in FIG. 16, the new frequency may be achieved by lowering the maximum setpoint on vacuum level selector 19. By lowering the maximum setpoint for vacuum level, the maximum peak is achieved more rapidly, causing valve 67 to cycle more frequently. Lowering the maximum setpoint on vacuum level selector 19 may also result in a slight decrease in the minimum vacuum level calculated by control circuit 69. The overall result is a more rapid fluttering type of suckling cycle, where the suction is more gentle and ranges between about 18 mmHg and 35 mmHg. The suction cycle is about 240 cycles per minute.

FIG. 19 shows another periodic vacuum pulse that may be achieved by a user programming the controls of an electric breast pump according to the invention. In this example, the frequency of the periodic vacuum pulse is approximately 45 cycles per minute. One way of achieving this frequency is by leaving vacuum level selector unchanged from its position in the example of FIG. 16, and adjusting vacuum rate selector 21 to a lower level. As vacuum rate selector 21 is lowered, the pump 51 slows down, and requires more time to achieve the maximum vacuum level in the breast cups, thereby lowering the frequency of the vacuum pulse. In addition, the amplitude of the vacuum pulse may be increased to a higher maximum level, which may also lower the vacuum pulse frequency. Adjusting vacuum level selector 19 to a higher level may also result in a slight increase in the minimum vacuum level calculated by control circuit 69. Thus, one or both of the manual controls 19 and 21 may be adjusted to achieve the pulse of FIG. 19. The overall result is a slower and deeper sucking cycle, which may range from about 25 mmHg to about 200 mmHg.

A programmable breast pump system according to the invention is not limited in operation to the foregoing examples of FIGS. 16-19. It should be readily appreciated that a user may adjust the vacuum level and vacuum rate controls to achieve a desired comfort level and/or tune the breast pump to the user's natural refractory time. The programmable controls also allow a user to make appropriate adjustments during a pumping session, for example, when the let-down reflex occurs, or as vacuum pressure requirements change as the session progresses.

Figure 20:
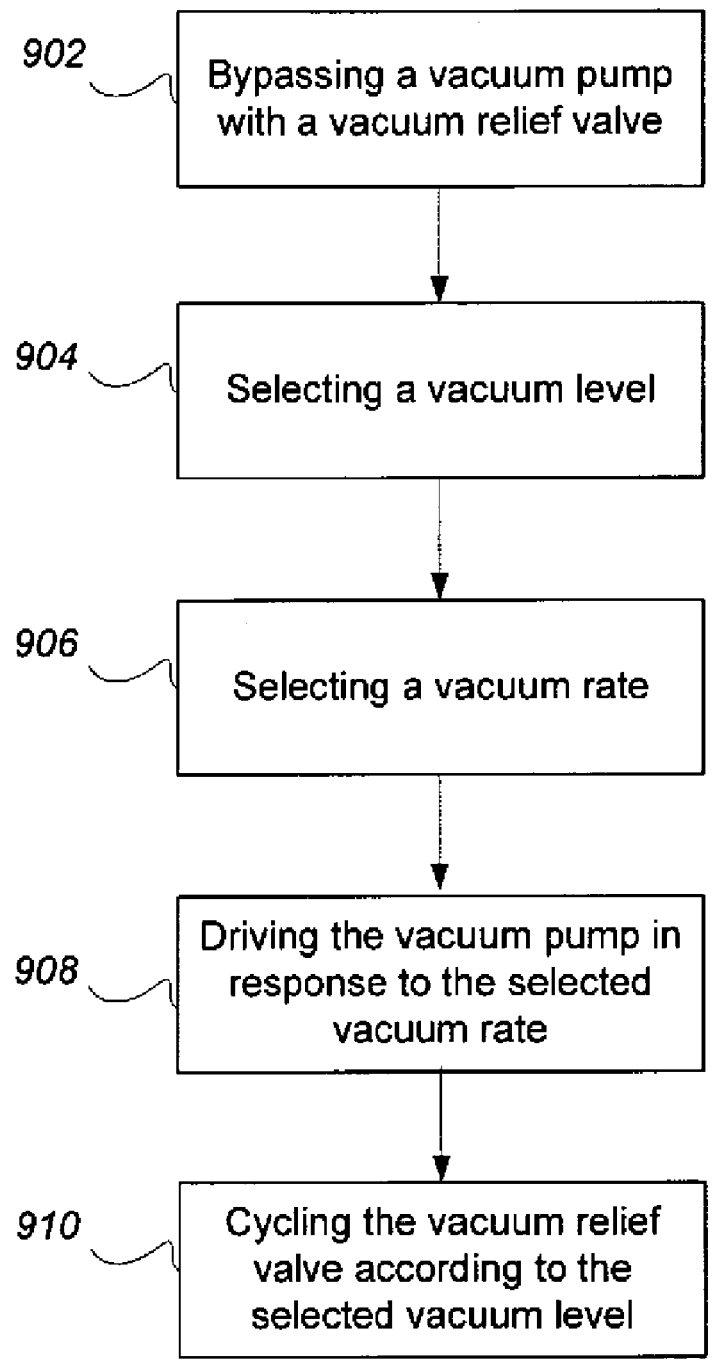
FIG. 20 is a process flow diagram of one embodiment of a method according to the invention for cycling vacuum pressure in a programmable electric breast pump.

The process flow chart of FIG. 20 illustrates one embodiment of a method 900 according to the invention for cycling vacuum pressure in a breast cup. In the process shown, it may be assumed that the breast cup chamber is pneumatically coupled to the inlet of a vacuum pump. The method begins with step 902, in which the vacuum pump is bypassed with a vacuum relief valve. In this step, bypassing the vacuum pump means that the vacuum relief valve is connected to the vacuum pump such that, when the valve is in one of two states (i.e. open or closed), the vacuum pump is not able to maintain a vacuum in the breast cup, and when the valve is in the other state, the vacuum pump is able to maintain or raise vacuum pressure in the breast cup.

The next step is step 904, in which a vacuum level is selected. In the next step 906, a vacuum rate is selected. These selecting steps 904 and 906 may be performed in any order. In one embodiment, either or both of these steps may be performed by a user adjusting the position of a manually operated selector. The selector may simply be toggled to an on position, or it may be adjusted to one of many possible positions. In another embodiment, selecting steps 904 and 906 may be performed automatically, for example, by a control circuit executing an algorithm.

Next, in step 908, the vacuum pump is driven in response to the selected vacuum rate. In one embodiment, the selected vacuum rate may correspond to the speed of a motor that is the prime mover for the vacuum pump. In the final step 910, the vacuum relief valve is cycled according to the selected vacuum level. In one embodiment, selecting the vacuum level in step 904 establishes a maximum setpoint for vacuum pressure in the breast cup. Then in step 910, the vacuum relief valve is actuated to relieve the vacuum pressure when it reaches the maximum. After a predetermined time period, the vacuum relief valve may be actuated again to allow vacuum pressure to build up. The predetermined time period may be set by a timing relay, or programmed, for example, in software executed by a control circuit. In this fashion, the vacuum relief valve is cycled according to the selected vacuum level. In another embodiment, selecting the vacuum level in step 904 establishes both a maximum and a minimum setpoint, allowing a controller to cycle the vacuum relief valve as vacuum pressure oscillates between the two setpoints.

Figure 21:
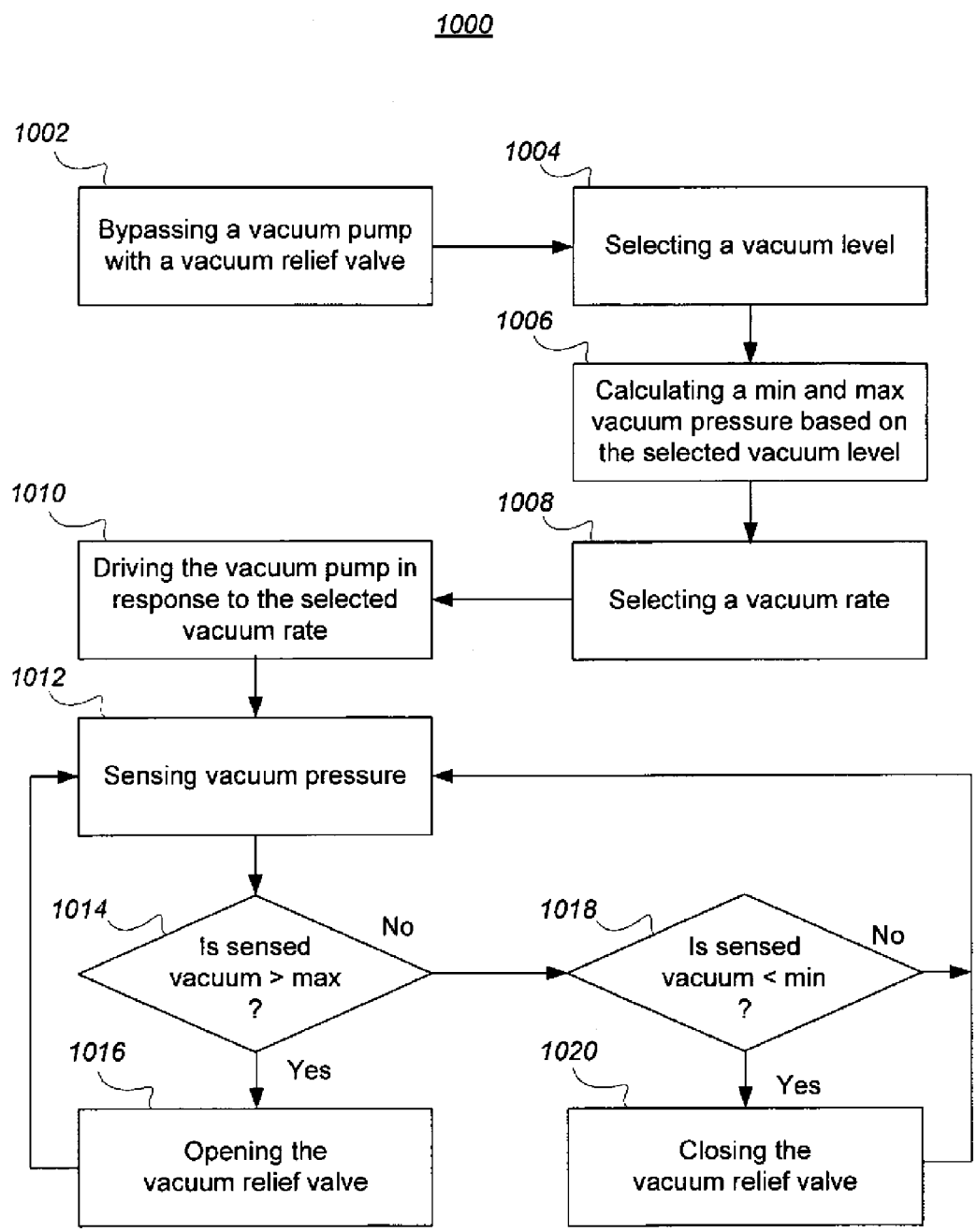
FIG. 21 is a process flow diagram of another embodiment of a method according to the invention for cycling vacuum pressure in a programmable electric breast pump.

FIG. 21 illustrates an embodiment of a method 1000 according to the invention, implicitly described in the context of the foregoing system embodiments, and provided here more explicitly in flow chart form. Method 1000 is a process for cycling vacuum pressure in a breast cup (or breast cup pair) that is pneumatically coupled to a vacuum pump. The method begins with step 1002, in which the vacuum pump is bypassed with a vacuum relief valve, as in step 902 of the previous embodiment. Next, in step 1004, a vacuum level is selected. This step may be performed using manual, automatic, or remote controls. In the next step 1006, a minimum vacuum pressure and a maximum vacuum pressure are calculated based on the vacuum level selected in the previous step. In one embodiment, the minimum and maximum levels may be calculated by a control circuit that executes an algorithm that is a function of variable input received from the selector. In another embodiment, the minimum level may be fixed at a predetermined value, while the maximum level may vary with the position of the selector. In another embodiment, the minimum and maximum levels change at different rates as the selected vacuum level changes.

The next step is step 1008, which is selecting a vacuum rate. This step may also be performed using manual, automatic, or remote controls. The next step 1010 is driving the vacuum pump in response to the selected vacuum rate. In one embodiment, this step is performed by varying the speed of a vacuum pump motor according to the selected vacuum rate, where a higher pump speed corresponds to a higher vacuum rate, and vice versa.

With the vacuum levels and vacuum rate selected, the method now progresses to its cycling steps. In step 1012, vacuum pressure is sensed in the breast cup(s). A decision block 1014 is then executed. In block 1014, it is determined whether the pressure sensed in step 1012 is greater than the maximum vacuum level. If so, the method continues on to step 1016. In step 1016, the vacuum relief valve is opened to relieve vacuum pressure, causing the vacuum pressure in the breast cup(s) to drop. The method then loops back to step 1012. If, however, in block 1014 it is determined that the pressure sensed in step 1012 is not greater than the maximum vacuum level, the method moves to step 1018.

Step 1018 is another decision block. It determines whether the vacuum level sensed in step 1012 is below the minimum vacuum level. If not, the method loops back to step 1012. If so, the method continues on to step 1020. In step 1020, the vacuum relief valve is closed, allowing vacuum pressure to build up in the breast cup(s). The method then loops back to step 1012.

Thus, once the process enters the cycling steps, it will follow a flow path through three possible process loops, where each process loop is initiated at step 1012 sensing a vacuum pressure. The first process loop occurs when the sensed vacuum pressure is greater than the calculated maximum level, in which case the method loops from step 1012 to 1014 to 1016 and back to 1012. The second process loop occurs when the sensed vacuum pressure lies between the calculated minimum and maximum levels, in which case the method loops from step 1012 to 1014 to 1018 and back to 1012. This loop may be executed any number of times in succession, as the vacuum pressure changes between its minimum and maximum set points. The third process loop occurs when the sensed vacuum pressure is less than the minimum level, in which case the method loops from step 1012 to 1014 to 1018 to 1020 and back to 1012. In this way, the process will cycle vacuum pressure in the breast cup(s) in a manner illustrated in FIGS. 16, 18 and 19. It should be recognized that steps 1014 and 1016 may be sequentially interchanged with blocks 1018 and 1020 without departing from the scope of the invention.

Figure 22:
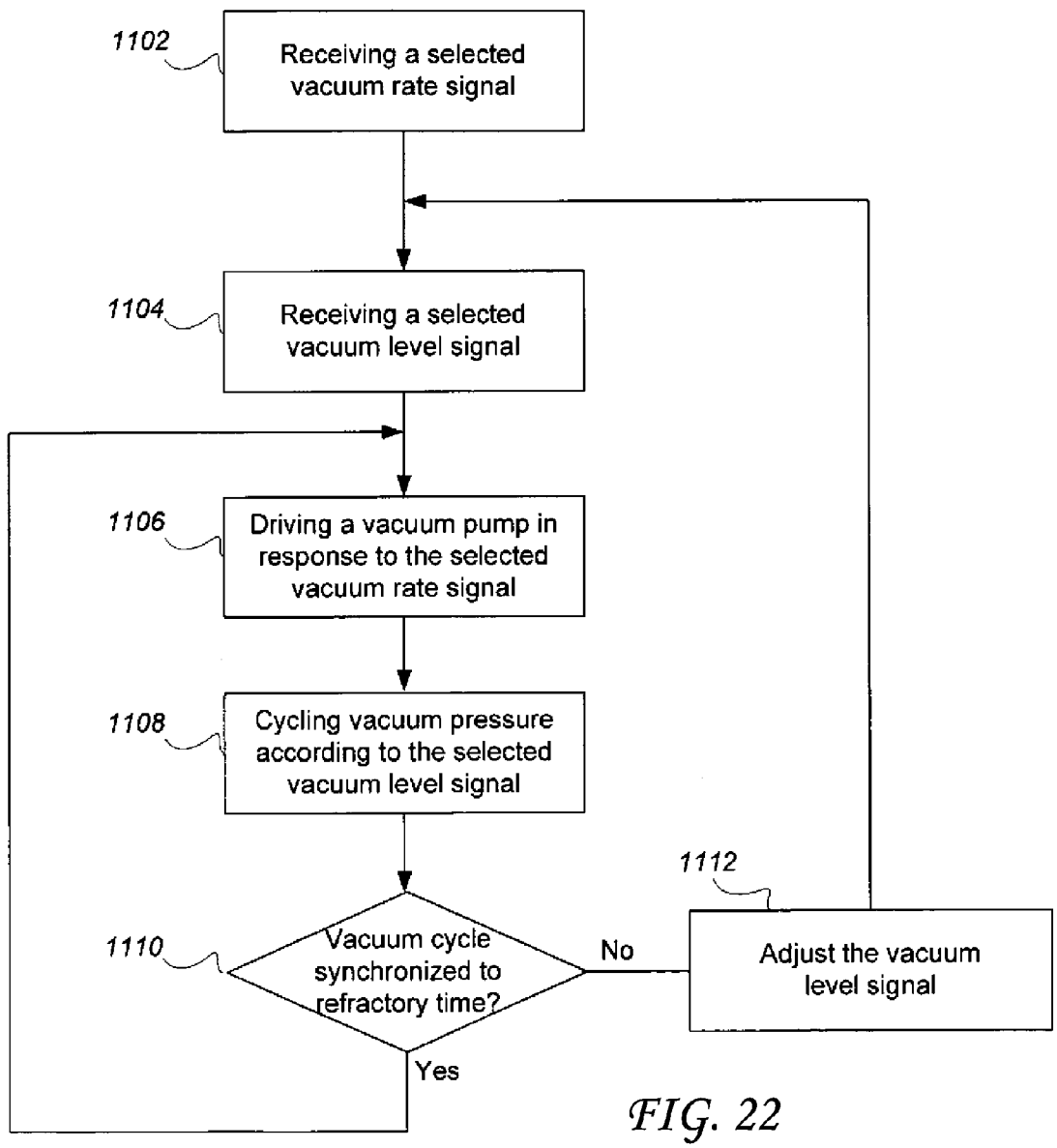
FIG. 22 is a process flow diagram of an embodiment of a method according to the invention for synchronizing cycling vacuum pressure in a programmable electric breast pump.

FIG. 22 illustrates a method 1100 according to the invention for synchronizing a breast pump with a natural refractory time of a breast. Method 1100 is an explicit process flow chart that captures another of many possible methods implicitly disclosed in the foregoing system embodiments. This method begins with step 1102, which is a step for receiving a selected vacuum rate signal. The next step 1104 is a step for receiving a selected vacuum level signal. Each of these first two steps may be performed by an automatic control circuit receiving input from a user manipulating a selector. The next step 1106 is driving a vacuum pump in response to the selected vacuum rate signal. This step may involve a control circuit issuing an output signal that controls the speed of the vacuum pump. Next, in step 1108, vacuum pressure is cycled in one or two breast cups that are pneumatically coupled to the vacuum pump. The cycling of the vacuum pressure is performed according to the selected vacuum level signal, as in previous embodiments.

In the next step, decision block 1110, it is determined whether the vacuum cycle is synchronized to, or in phase with, the natural refractory time. Preferably, this decision is resolved by the user according to her preference. If the vacuum cycle is not synchronized, the method progresses to a feedback loop through step 1112. In step 1112, the vacuum level signal is adjusted. The method then returns to step 1104. At step 1108, the vacuum pressure cycle changes according to the adjustment made in step 1104, i.e. adjusting the vacuum level signal in step 1104 changes the maximum and/or minimum setpoints, which, at a constant vacuum rate, changes the frequency of the vacuum pulse. Decision block 1110 may then be resolved again, and the feedback loop repeated as necessary until synchronization is achieved. At that point, the method loops back to step 1106, and the vacuum pump is driven according to the selected vacuum rate.

In another embodiment, steps 1102 and 1104 may be sequentially interchanged, in which case, step 1112 is provided to adjust the vacuum rate signal. In another embodiment, two adjustment steps may be included in the feedback loop, one for adjusting the vacuum level signal, and another for adjusting the vacuum rate signal. In this case, the feedback loop returns to step 1102.

It should be appreciated that the foregoing methods create an refractory time in an automatic breast pump system by cycling a vacuum pulse according to a selectable vacuum rate and selectable vacuum levels. These features enable a user to program the breast pump for maximum comfort, or to synchronize the pulse of the breast pump with a natural refractory time to optimize the efficiency of a milk expressing session.

The electric pump and breast system described above provides a novel combination of breast pump control and breast cup to mimic an action of a suckling infant.

While the invention herein disclosed has been described by means of specific embodiments and applications thereof, numerous modifications and variations could be made thereto by those skilled in the art without departing from the scope of the invention set forth in the claims.

We claim:

1. A breast pump system comprising:
   a breast cup assembly having:
   an attachment end for connecting to a vacuum source;
   a large open end opposite the attachment end for accepting a woman's breast:
   a holder of the breast cup assembly comprising:
   a small end residing proximal to the attachment end of the breast cup assembly and including a holder engaging feature;
   a large end opposite the small end and having a larger diameter than the small end; and
   a center portion connecting the small end to the large end, the center portion having at least one cut out passing radially through the holder to allow air to freely pass through the holder;
   a collapsible breast cup of the breast cup assembly, the collapsible breast cup made of biocompatible material and having varying thickness to cause the breast cup to collapse in a manner to mimic an action of a suckling infant, the breast cup directly connected to the vacuum source and having an inner surface exposed to vacuum from the vacuum source and an outer surface exposed to atmospheric pressure, the breast cup sequentially comprising:
   a connecting portion including a cup engaging feature engaged by the holder engaging feature of the small end of the holder for retaining the breast cup in the holder, the connecting portion connectable to the vacuum source;
   a collapsible cylindrical middle portion formed contiguous to the connecting portion, and configured for receiving a teat of a breast and having a first thickness; and
   a collapsible cone shaped portion formed contiguous to the cylindrical middle portion and configured for receiving an areola of the breast, a small diameter portion of the cone shaped portion proximal to the cylindrical middle portion having a second thickness and a larger diameter portion of the cone shaped portion opposite the cylindrical middle portion having a third thickness, wherein the second thickness is less than the first thickness and the third thickness is approximately equal to the first thickness so that upon application of vacuum to the connecting portion, the cone shaped portion collapses on the areola of the breast before the cylindrical middle portion collapses on the teat of the breast;

a container connected to the breast cup for collecting breast milk;

a vacuum line with a first and second end, the first end being connected to the breast cup to provide the vacuum source;

a breast pump having an inlet, the inlet being attached to the second end of the vacuum line for drawing a vacuum in the breast cup, thereby causing milk to be extracted from the breast; and a control circuit controlling a vacuum level provided by the breast pump to the breast cup, the control circuit controlling the breast pump to establish a pumping rate, a maximum vacuum level, and a minimum vacuum level, wherein the vacuum level increases as a function of the pumping rate until the maximum vacuum level is reached, then the vacuum level drops until the vacuum level is less than the minimum vacuum level, and then the vacuum level increases again as a function of the pumping rate until the maximum vacuum level is again reached, thereby mimicking an action of a suckling infant.

2. The breast pump system of claim 1, wherein the breast pump includes a control for use by a user to select the maximum vacuum level.

3. The breast pump system of claim 1, wherein the breast pump includes a second control for use by the user to select the pumping rate.

4. The breast pump system of claim 1, wherein the breast pump includes:
a vacuum pump having an inlet and an outlet;
shunt connecting the inlet to the outlet; and
a valve in the shunt, the valve opened by the control circuit to reduce the vacuum level provided to the breast cup and the valve closed by the control circuit to increase the vacuum level provided to the breast cup.

5. The breast pump system of claim 1, further including a unidirectional filter connected in series in the vacuum line between the breast cup and the breast pump allowing a flow towards the breast pump and preventing a flow towards the breast cup, for preventing contamination between the pump and the breast cup.

6. The breast pump system of claim 1, wherein the unidirectional filter is a biological unidirectional filter.

7. The breast pump system of claim 1, wherein the part of the cone shaped portion having the second thickness is closest to the cylindrical middle area, and the cone shaped portion thickens away from the cylindrical middle area.

8. The breast pump system of claim 1, wherein the second thickness is approximately 0.03 inches and the first thickness is approximately 0.1 inches so that upon application of vacuum to the connecting portion the cone shaped portion distorts before the mid portion distorts.

9. The breast pump system of claim 1, wherein the second thickness is approximately $\frac{1}{3}$ of the first thickness so that upon application of vacuum to the connecting portion the cone shaped portion distorts before the mid portion distorts.

10. The breast pump system of claim 1, wherein the holder is not exposed to vacuum from the vacuum source.

11. The breast pump system of claim 1, wherein the second thickness is about 30 percent of the first thickness.

12. The breast pump system of claim 1, wherein the first thickness is approximately 0.1 inches and the second thickness is approximately 0.03 inches.

13. The breast pump system of claim 1, wherein the holder engaging feature and the cup engaging feature include engaging surfaces orthogonal to a centerline of the cylindrical middle portion to resist withdrawal of the breast cup from the holder.

14. The breast pump system of claim 1, wherein breast cup is a single layer breast cup.

15. The breast pump system of claim 1, wherein portions of the breast cup between the connecting portion and an outer portion of the cone shaped portion are not connected to the holder.

16. The breast pump system of claim 1, wherein portions of the breast cup between the connecting portion and a platform proximal to an outer edge of the cone shaped portion are free to move within the holder.

17. A breast pump system comprising:
a breast cup assembly having:
an attachment end for connecting to a container connected to the breast pump assembly for collecting breast milk and connecting to a vacuum source;
a large open end opposite the attachment end for accepting a woman's breast:
a holder of the breast cup assembly comprising:
a small end residing proximal to the attachment end of the breast cup assembly and including a holder engaging feature;
a large end opposite the small end and having a larger diameter than the small end; and
a center portion connecting the small end to the large end, the center portion having at least one cut out passing radially through the holder to allow air to freely pass through the holder;
a collapsible breast cup of the breast cup assembly made of biocompatible material, the breast cup having an inner surface exposed to the vacuum source and an outer surface exposed to atmospheric pressure, the breast cup sequentially comprising:
a connecting portion engagable with the holder engaging feature and connectable to the vacuum source;
a cylindrical middle portion formed contiguous to the connecting portion, and configured for receiving a teat of a breast and having a first thickness; and
a cone shaped portion formed contiguous to the cylindrical middle portion, and configured for receiving a portion of the breast, the cone shaped portion increasing in diameter away from the cylindrical middle portion to the large open end, the cone shaped portion having a second thickness thinner than the first thickness in a small diameter portion of the cone shaped portion proximal to the cylindrical middle portion and increasing in diameter away from the cylindrical middle portion towards the large open end, wherein the second thickness is less than the first thickness so that upon application of vacuum to the connecting portion the cone shaped portion collapses before the mid portion collapses;
a vacuum line providing the vacuum source and having a first and second end, the first end being connected to the breast cup assembly;

a breast pump having an inlet, the inlet being attached to the second end of the vacuum line for drawing a vacuum in the breast cup, thereby causing milk to be extracted from the breast; and a control circuit controlling a vacuum level provided by the breast pump to the breast cup, the control circuit controlling the breast pump to establish a pumping rate, a maximum vacuum level, and a minimum vacuum level, wherein the vacuum level increases as a function of the pumping rate until the maximum vacuum level is reached, then the vacuum level drops until the vacuum level is less than the minimum vacuum level, and then the vacuum level increases again as a function of the pumping rate until the maximum vacuum level is again reached, therein the combination of the collapsing breast cup and the vacuum level and rate controllable breast pump mimics an action of a suckling infant.

18. The breast pump system of claim 17, wherein the vacuum line connects the vacuum pump to the container and the container is in fluid communication with the connection portion of the breast cup.

19. The breast pump system of claim 17, wherein all surfaces of the holder are exposed to ambient pressure.

20. A breast pump system comprising:
a breast cup assembly having:
   an attachment end for connecting to a vacuum source;
   a large open end opposite the attachment end for accepting a woman's breast:
a holder of the breast cup assembly comprising:
   a small end residing proximal to the attachment end of the breast cup assembly and including a holder engaging feature;
   a large end opposite the small end and having a larger diameter than the small end; and
   a center portion connecting the small end to the large end, the center portion having at least one cut out passing radially through the holder to allow air to freely pass through the holder;
a collapsible single layer breast cup of the breast cup assembly made of biocompatible material, the breast cup having an inner surface exposed to vacuum and an outer surface exposed to atmospheric pressure, the breast cup sequentially comprising:
   a connecting portion engagable with the holder engaging feature and connectable to a vacuum source;
   a cylindrical middle portion formed contiguous to the connecting portion, and configured for receiving a teat of a breast and uniformly having a first thickness of approximately 0.1 inches; and
   a cone shaped portion formed contiguous to the cylindrical middle portion, and configured for receiving a portion of the breast, the cone shaped portion increasing in diameter away from the cylindrical middle portion to a large open end, the cone shaped portion thickness is approximately 0.03 inches closest to the cylindrical middle portion, and the cone shaped portion thickens away from the cylindrical middle a portion to a thickness of approximately 0.1 inches,
   wherein the relative thickness of the cylindrical middle portion and the cone shaped portion are selected so that upon application of vacuum to the connecting portion the cone shaped portion collapses before the cylindrical middle portion collapses;
a container connected to the breast cup assembly for collecting breast milk;
a breast pump having an inlet in fluid communication with the vacuum source for drawing a vacuum in the breast cup, thereby causing milk to be extracted from the breast; and
a control circuit controlling a vacuum level provided by the breast pump to the breast cup, the control circuit controlling the breast pump to establish a pumping rate, a maximum vacuum level, and a minimum vacuum level, wherein the vacuum level increases as a function of the pumping rate until the maximum vacuum level is reached, then the vacuum level drops until the vacuum level is less than the minimum vacuum level, and then the vacuum level increases again as a function of the pumping rate until the maximum vacuum level is again reached, therein the combination of the collapsing breast cup and the vacuum level and rate controllable breast pump mimics an action of a suckling infant.

* * * * *